(12) United States Patent
Al Juhaiman et al.

(10) Patent No.: US 9,894,896 B2
(45) Date of Patent: Feb. 20, 2018

(54) METHOD OF USING A CLAY SUSPENSION TO PREVENT VIRAL AND PHYTOPLASMA DISEASES IN PLANTS

(71) Applicant: KING SAUD UNIVERSITY, Riyadh (SA)

(72) Inventors: Layla Abdulkareem Al Juhaiman, Riyadh (SA); Nagwa Mohamed Mohamed Amin Aref, Riyadh (SA); Waffa Kotb Mekhamer, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 14/735,092

(22) Filed: Jun. 9, 2015

(65) Prior Publication Data

US 2016/0360755 A1 Dec. 15, 2016

(51) Int. Cl.
*A01N 25/04* (2006.01)
*A01N 59/06* (2006.01)

(52) U.S. Cl.
CPC .................................. *A01N 25/04* (2013.01)

(58) Field of Classification Search
None
See application file for complete search history.

(56) References Cited

U.S. PATENT DOCUMENTS

2010/0040650 A1 2/2010 Ren et al.
2011/0301369 A1 12/2011 Lin et al.

FOREIGN PATENT DOCUMENTS

WO  WO 2010/063998  6/2010

OTHER PUBLICATIONS

Retsch (2015), Planetary Ball Mill PM 100, pp. 1-7.*
Bertaccini et al., Phytoplasma and phytoplasma diseases: a review of recent research, Phtyopathol. Mediterr. (2009), vol. 48, pp. 355-378.*
Al-Shahrani (Water Pollution X (2010)), Abstract.*
Ebrahim-Nesbat et al., (Phytopathologishce Zeitschrift (1972), Abstract.*
Yoshizaki (Journal of the Hokkaido University of Education Section II B (1985)), Abstract.*
Hecht-Poinar et al. (Virology (1966)), Abstract.*
Rhim et al., Tensile Water Vapor Barrier and Antimicrobial Properties of PLA/Nanoclay Composite Films, Food Science and Technology, 42, 612-617, 2009.

* cited by examiner

*Primary Examiner* — Hasan S Ahmed
*Assistant Examiner* — Frank Choi
(74) *Attorney, Agent, or Firm* — Richard C. Litman (57) ABSTRACT

The method of using a clay suspension to prevent viral and phytoplasma diseases in plants includes administering a clay suspension to the plant, such as through spraying the plant's leaves or soaking the plant's nursery shoots with the clay suspension. The clay suspension is applied to the plant to prevent the viral or phytoplasma disease prior to planting the plant in its nursery shoot stage. The clay suspension is preferably formed from natural clay suspended in water (1% w/v). The clay may be in either its natural form, or may be in the form of clay nanoparticles suspended in water. For a suspension formed from clay nanoparticles, the clay nanoparticles may be separated by sedimentation in distilled water.

4 Claims, 12 Drawing Sheets

| Treatments \ No. of plants | 1 | 2 | 3 | 4 | Average % |
|---|---|---|---|---|---|
| Healthy | 0 | 0 | 0 | 0 | 0 |
| 1% Raw clay Sparing Application on the leaves before virus inoculation | | | | | |
| Inoculated with TMV only. | 12 | 32 | 18 | 12 | 18.5% |
| Spraying application with 1% Raw Clay only. | 0 | 0 | 0 | 0 | 0 |
| Spraying application with 1% Raw Clay particles before virus inoculation. | 6 | 2 | 3 | 2 | 3.25% |
| Nano Clay Spraying Application on the leaves before virus inoculation | | | | | |
| No. of L.L./No. of inoculated Leaves with virus only. | 77/9 | 14/9 | 14/9 | 6/9 | 27.75% |
| No. of infected leaves /No. of inoculated Leaves with virus only. | 9/9 | 6/9 | 3/9 | 2/9 | 20/36 |
| Spraying application with nano Clay only. | 0 | 0 | 0 | 0 | 0 |
| No. of L.L./No. of treated Leaves with Nano Clay+Virus | 12/9 | 0/9 | 4/9 | 14/9 | 7.5% |
| No. of infected leaves /No. of treated Leaves with Nano Clay and Virus. | 2/9 | 0/9 | 2/9 | 4/9 | 8/36 |

*Fig. 1*

| Treatments | 1-Healthy | 2. Infected with virus | 3. Clay-c(virus) | 4. Virus-cl(clay) | 5. Mix(clay+virus) |
|---|---|---|---|---|---|
| TAILED CELLS% | 5 | 17 | 12 | 15 | 14 |
| UNTAILED CELLS% | 95 | 83 | 88 | 85 | 86 |
| TAIL LENGTH μm | 1.87 | 3.84 | 3.16 | 3.22 | 3.33 |
| TAIL DNA % | 1.92 | 4.09 | 3.51 | 3.67 | 3.44 |
| TAIL MOVEMENT UNIT | 3.590 | 15.706 | 11.092 | 11.817 | 11.455 |

Fig. 2

| Treatments | 1.Healthy | 2.TMV | 3.Pretreatment | 4.Post treatment | 5.Neutralized |
|---|---|---|---|---|---|
| Total DNA in μg/gm | 298.94 | 259.84 | 278.89 | 264.93 | 281.21 |

| Treatments | Healthy | TMV | Pretreatment | Post Treatments | Neutralized |
|---|---|---|---|---|---|
| Chlorophyll-a | 2.24 | 1.59 | 1.87 | 1.65 | 1.98 |
| Chlorophyll-b | 1.575 | 0.87 | 1.16 | 0.92 | 1.23 |
| Total Protein | 3.79 | 3.08 | 3.35 | 3.28 | 3.41 |

METHOD OF USING A CLAY SUSPENSION TO PREVENT VIRAL AND PHYTOPLASMA DISEASES IN PLANTS

BACKGROUND OF THE INVENTION

1. Field of the Invention

The present invention relates to methods for preventing disease in plants, and particularly to prevention of viruses and phytoplasma diseases in plants by use of a clay suspension.

2. Description of the Related Art

Plants which are grown on agricultural land or in general households are often infected with plant viruses or phytoplasma. As a result, the value of production amounts, plant appearance, or other desirable factors may be markedly decreased. Plant diseases may cause serious damage to important crops, such as grains, vegetables and fruit trees. Many viruses, for example, which have invaded plant cells replicate by relying on the metabolisms of the host plants as an obligate parasite. For this reason, it is difficult to specifically inhibit only the replication of the viruses while maintaining the normal metabolic pathways in the plants.

Many of the traditional agents for controlling or preventing plant disease suffer from numerous problems, including insufficient inhibitive effects against plant diseases and toxicity to both animals and plants. Many of the drugs or agents for inhibiting microorganisms or viruses, including pesticides for use on growing plants and preservatives for agricultural and livestock products, are not only toxic to humans but also destructive to the environment.

Thus, a method of using a clay suspension to prevent viral and phytoplasma diseases in plants solving the aforementioned problems is desired.

SUMMARY OF THE INVENTION

The method of using a clay suspension to prevent viral and phytoplasma diseases in plants includes administering a clay suspension to the plant, such as through spraying the plant's leaves or soaking the plant's nursery shoots with the clay suspension. Preferably, the clay suspension is applied to prevent the viral or phytoplasma disease prior to planting the plant in its nursery shoot stage. The clay suspension is preferably formed from natural clay suspended in water (1% w/v). The clay may be in either its natural form, or may be in the form of clay nanoparticles (i.e., nano-sized clay particles). For a suspension formed from clay nanoparticles, the clay nanoparticles may be separated by sedimentation in distilled water. Since the suspension is prepared using only clay and water, the suspension is free from toxic solvents and harmful chemicals. As such, the clay suspension can be safely used for agricultural purposes.

These and other features of the present invention will become readily apparent upon further review of the following specification and drawings.

BRIEF DESCRIPTION OF THE DRAWINGS

FIG. 12B is a transmission electron micrograph at high magnification by Transmission Electron Microscope (TEM)

of the fibril structure inside the vesicular parts around an infected cell, with phytoplasma associated with clay particles.

DETAILED DESCRIPTION OF THE PREFERRED EMBODIMENTS

The method of using a clay suspension to prevent viral and phytoplasma diseases in plants includes administering a clay suspension to the plant, such as through spraying the plant's leaves or soaking the plant's nursery shoots (i.e., the external nursery or growth support for the plant) with the clay suspension, resulting in a reduction or prevention of viral and/or pleomorphic phytoplasma diseases in plants. Preferably, the clay suspension is applied to prevent the viral or phytoplasma disease prior to planting the plant in its nursery shoot stage. The clay suspension is preferably formed from natural clay suspended in water (1% w/v). The clay may be in either its natural form, or may be in the form of clay nanoparticles suspended in water. For a suspension formed from clay nanoparticles, the clay nanoparticles may be separated by sedimentation in distilled water, where the clay nanoparticles preferably have diameters ranging between approximately 200 nm and approximately 300 nm. Since the suspension is prepared using only clay and water, the suspension is free from toxic solvents and harmful chemicals. As such, the clay suspension can be safely used for agricultural purposes.

As will be described in detail below, the method of using a clay suspension to prevent viral and phytoplasma diseases in plants has been experimentally found to suppress virus particles, enhance natural plant metabolic growth, and totally dissolve the phytoplasma cell inside the infected phloem of a plant. Administration of the clay suspension can include application of the clay suspension on a plant surface, such as by spraying or wiping the clay suspension on a plant part, e.g., the leaves of the plant. Administration of the clay suspension may alternatively be performed by soaking the plant in the clay suspension, such as by soaking the aerial parts of the nursery shoots in the clay suspension. For the soaking of nursery shoots, the nursery shoots of the plant may be soaked in the clay suspension for approximately seven to approximately ten days.

Figure 1:
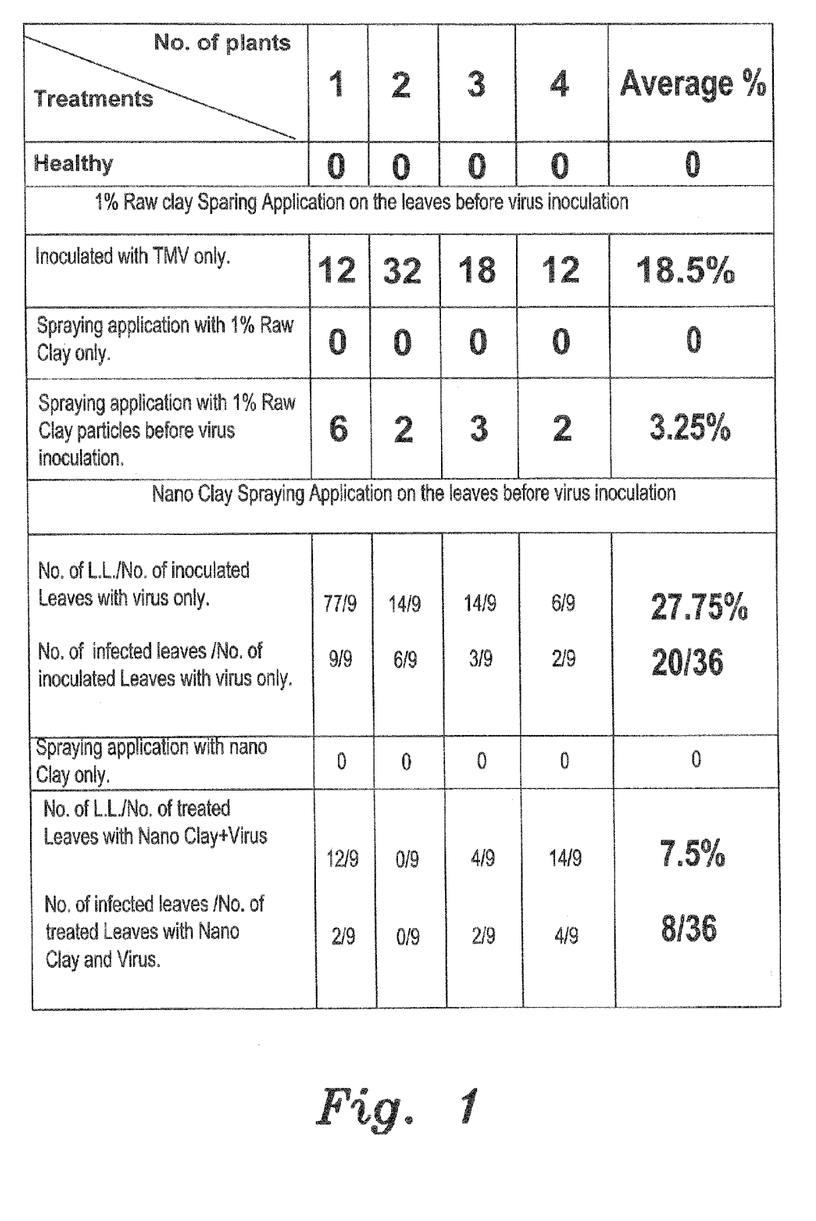
FIG. 1 is a table showing results of a method of using a clay suspension to prevent viral diseases in plants according to the present invention, particularly by spraying a clay suspension, formed from either clay in its natural state or clay nanoparticles, on a *Datura metel* plant, where the reduction of virus infection is measured by local lesion forming unit percentage (LLFU %).

Further, as will be described in detail below, experiments have shown that spraying the leaves of a *Datura metel* plant with the clay suspension before or after virus inoculation resulted in a significant decrease in the number of infected leaves, measured by factors such the plant exhibiting local necrotic lesions. Experiments were performed with the Tobacco Mosaic Virus (TMV). As shown in the table of FIG. 1, spray application of the clay suspension induced reduction in virus infectivity. Application of a 1% w/v clay suspension formed from clay in its natural state resulted in a decrease in virus infectivity from 18.5% to 3.25%, and application of a clay suspension from clay nanoparticles resulted in a decrease in virus infectivity from 27.75% to 7.5%. The table of FIG. 1 shows the experimental results of the method of using a clay suspension to prevent viral diseases in plants, where the reduction of virus infection is measured by local lesion forming unit percentage (LLFU %).

It is believed that viruses attach to the solid surfaces of clay particles in the suspension, thus causing the clay particles to act like a sink for the virus particles. It is possible that at least a portion of reversibly attached virus particles become irreversibly attached to the clay with time, according to the principles of quasi-equilibrium adsorption and surface sink (QEASS). This dynamic interaction between the virus and clay surface can result in inactivation of the in bulk fluid at the solid-liquid interface.

Figure 2:
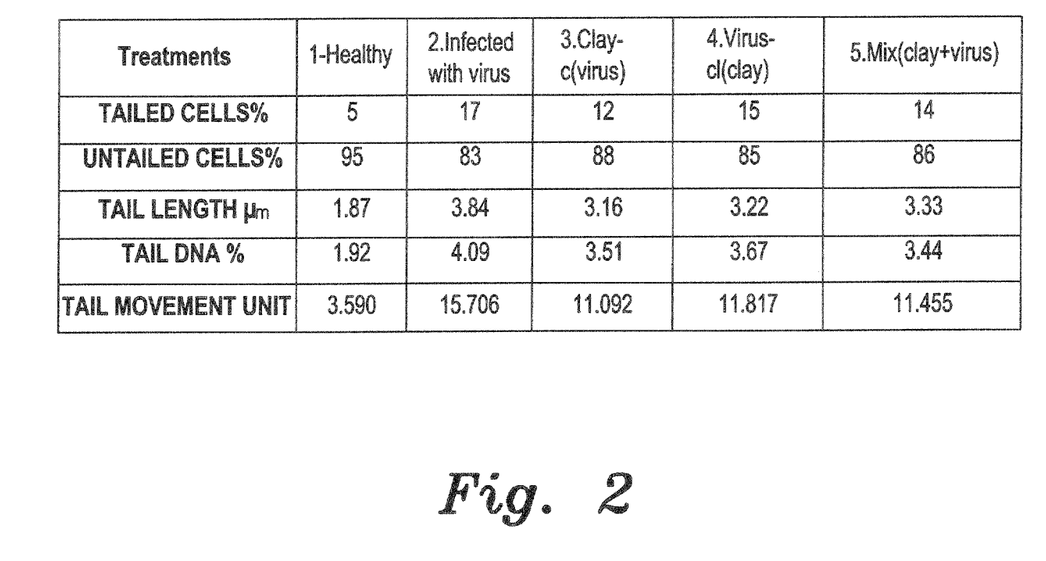
FIG. 2 is a table showing DNA damage in five treatment groups of plants, measured by comet assay, specifically comparing healthy plants, plants infected with a virus, plants treated with the method of using a clay suspension to prevent viral diseases in plants prior to infection with the virus, plants treated with the method of using a clay suspension to prevent viral diseases in plants following infection with the virus, and plants simultaneously treated with the clay suspension and the virus.
Figure 3A:
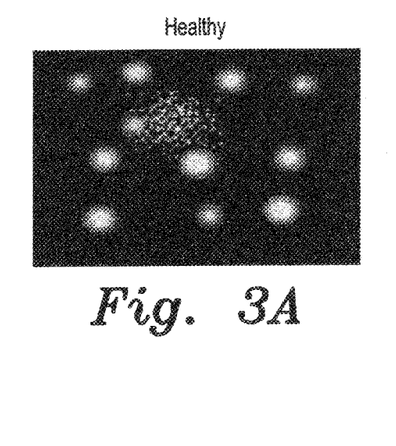
FIG. 3A shows the DNA damage measured by the comet assay for the healthy treatment group of FIG. 2.
Figure 3B:
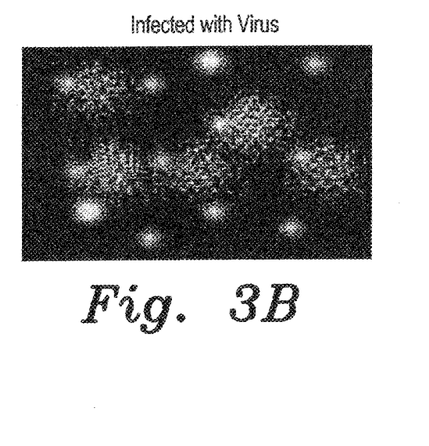
FIG. 3B shows the DNA damage measured by the comet assay for the infected treatment group of FIG. 2.
Figure 3C:
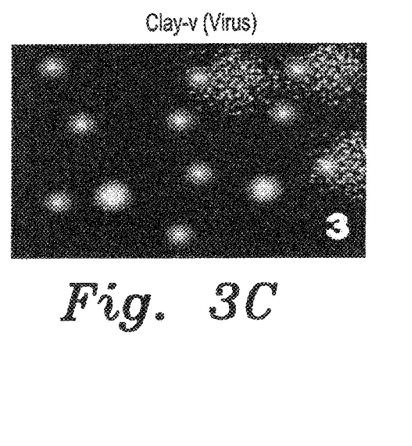
FIG. 3C shows the DNA damage measured by the comet assay for the treatment group of FIG. 2 treated with the method of using a clay suspension to prevent viral diseases in plants prior to infection with the virus.
Figure 3D:
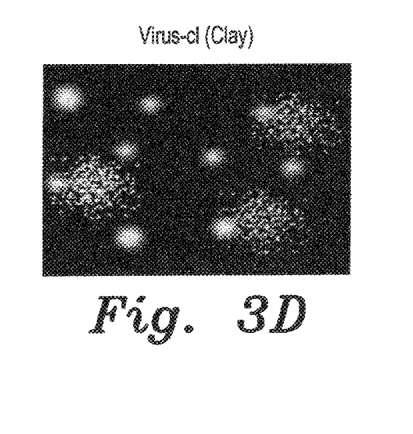
FIG. 3D shows the DNA damage measured by the comet assay for the treatment group of FIG. 2 treated with the method of using a clay suspension to prevent viral diseases in plants following infection with the virus.
Figure 3E:
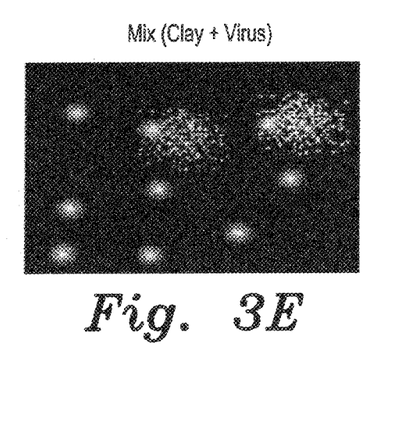
FIG. 3E shows the DNA damage measured by the comet assay for the treatment group of FIG. 2 simultaneously treated with the clay suspension and the virus.
Figure 4:
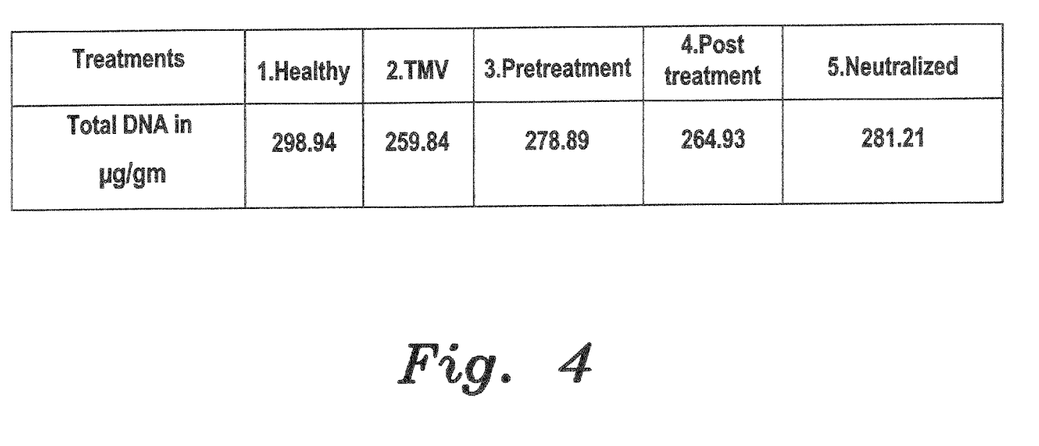
FIG. 4 is a table comparing total DNA content in detached leaves of the *Datura metel* plant in the five treatment groups of FIG. 2.
Figure 5:
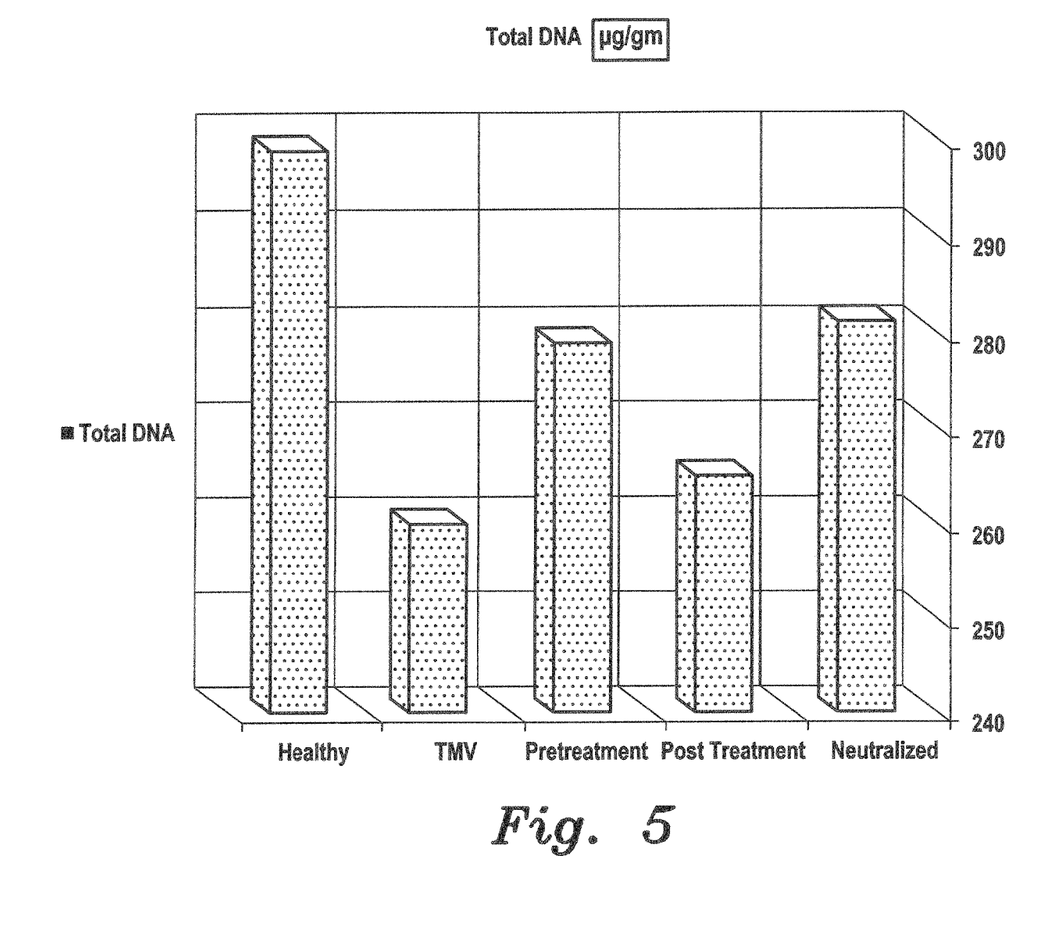
FIG. 5 is a histogram showing total DNA content in the detached leaves of the *Datura metel* plant in the five treatment groups of FIGS. 2 and 4.
Figure 6:
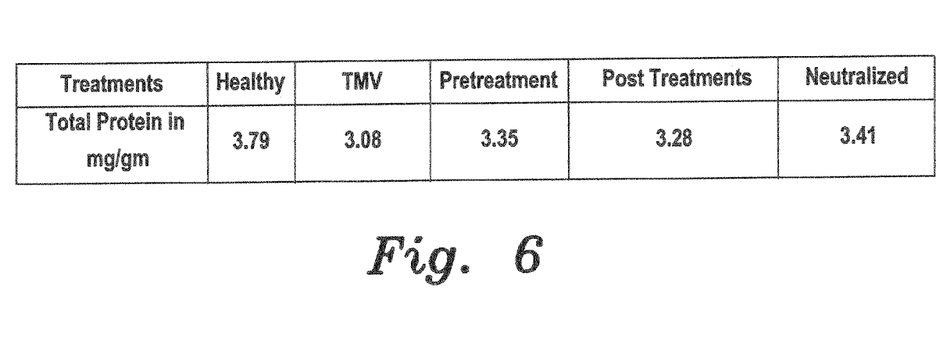
FIG. 6 is a table comparing the total protein content in the detached leaves of the *Datura metel* plant in the five treatment groups of FIGS. 2 and 4.
Figure 7:
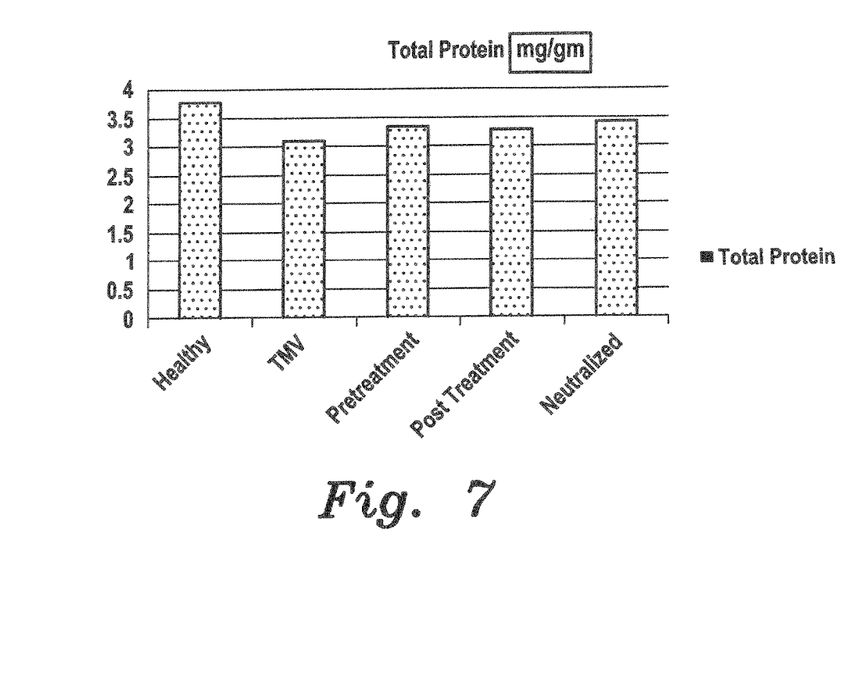
FIG. 7 is a graph comparing the total protein content in the detached leaves of the *Datura metel* plant in the five treatment groups of FIGS. 2 and 4.
Figure 8:
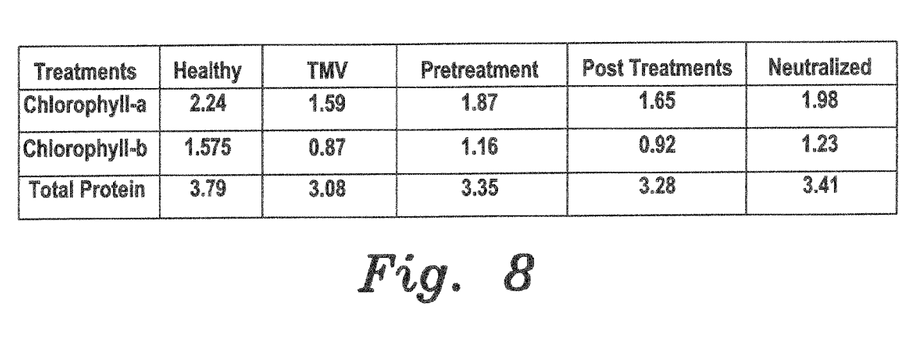
FIG. 8 is a table comparing chlorophyll-a, chlorophyll-b and total protein concentration in mg/g for the detached leaves of the *Datura metel* plant in the five treatment groups of FIGS. 2 and 4.
Figure 9:
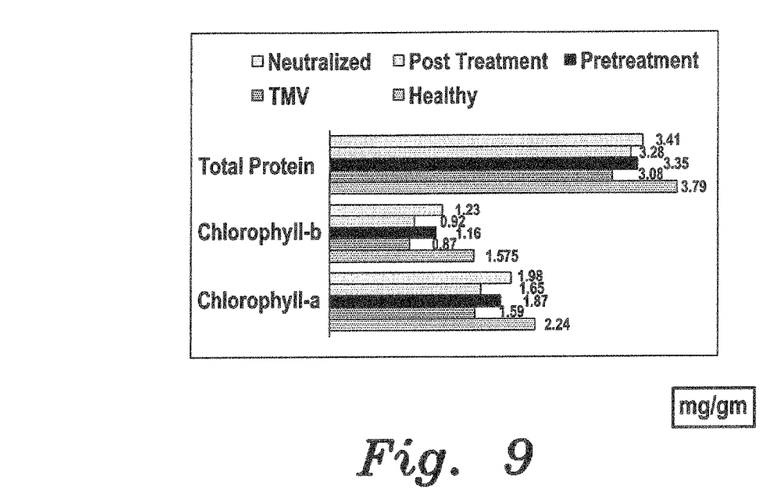
FIG. 9 is a graph comparing chlorophyll-a, chlorophyll-b and total protein concentration in mg/g for the detached leaves of the *Datura metel* plant in the five treatment groups of FIGS. 2 and 4.

Furthermore, improvement in metabolism in infected detached leaves of the *Datura metel* plant upon treatment with 1% w/v clay suspension was demonstrated by an increase in total DNA content, total protein content, and in the amount of chlorophyll-a and chlorophyll-b, as shown in FIGS. 2-9. As application of the clay suspension also exhibited an improvement in plant metabolism of infected plants, the clay suspension is also found to be useful for treating infected plants. The table of FIG. 2 shows DNA damage in five treatment groups of plants, measured by comet assay, specifically comparing healthy plants, plants infected with a virus, plants treated with the method of using a clay suspension to prevent viral diseases in plants prior to infection with the virus, plants treated with the method of using a clay suspension to prevent viral diseases in plants following infection with the virus, and plants simultaneously treated with the clay suspension and the virus. FIG. 3A shows the DNA damage measured by the comet assay for the healthy treatment group of FIG. 2; FIG. 3B shows the DNA damage measured by the comet assay for the infected treatment group of FIG. 2; FIG. 3C shows the DNA damage measured by the comet assay for the treatment group of FIG. 2 treated with the method of using a clay suspension to prevent viral diseases in plants prior to infection with the virus; FIG. 3D shows the DNA damage measured by the comet assay for the treatment group of FIG. 2 treated with the method of using a clay suspension to prevent viral diseases in plants following infection with the virus; and FIG. 3E shows the DNA damage measured by the comet assay for the treatment group of FIG. 2 simultaneously treated with the clay suspension and the virus. FIGS. 4 and 5 compare total DNA content in detached leaves of the *Datura metel* plant in the five treatment groups of FIG. 2. FIGS. 6 and 7 compare the total protein content in the detached leaves of the *Datura metel* plant in the five treatment groups of FIGS. 2 and 4. FIGS. 8 and 9 compare chlorophyll-a, chlorophyll-b and total protein concentration in mg/g for the detached leaves of the *Datura metel* plant in the five treatment groups of FIGS. 2 and 4.

DNA damage was measured by calculating the length of the tail and percentage of total DNA in the tail in the five treatment groups on the detached leaves of the *Datura metel* plant. Higher tail moments were indicative of greater DNA damage. The total DNA contents demonstrated that treatment with the clay suspension was effective in repairing virus infection. With regard to FIGS. 6 and 7, which show total protein contents in the *Datura metel* detached leaves in the five treatment groups, the total protein contents demonstrated that the clay suspension was effective in repairing virus infection.

The effect of the clay suspension as an anti-phytoplasma agent was studied by soaking lemon nursery shoots in a water solution including 1% w/v clay suspension for one week. Ultrastructure examination of the soaked infected lemon nursery shoots compared to non-soaked control shoots, using TEM, showed dissociation of the phytoplasma pleomorphic bodies inside the vascular cells. The membranes were tiered inside the infected vascular cells that were associated with the incidence of distributed clay particles in their natural state.

Figure 10:
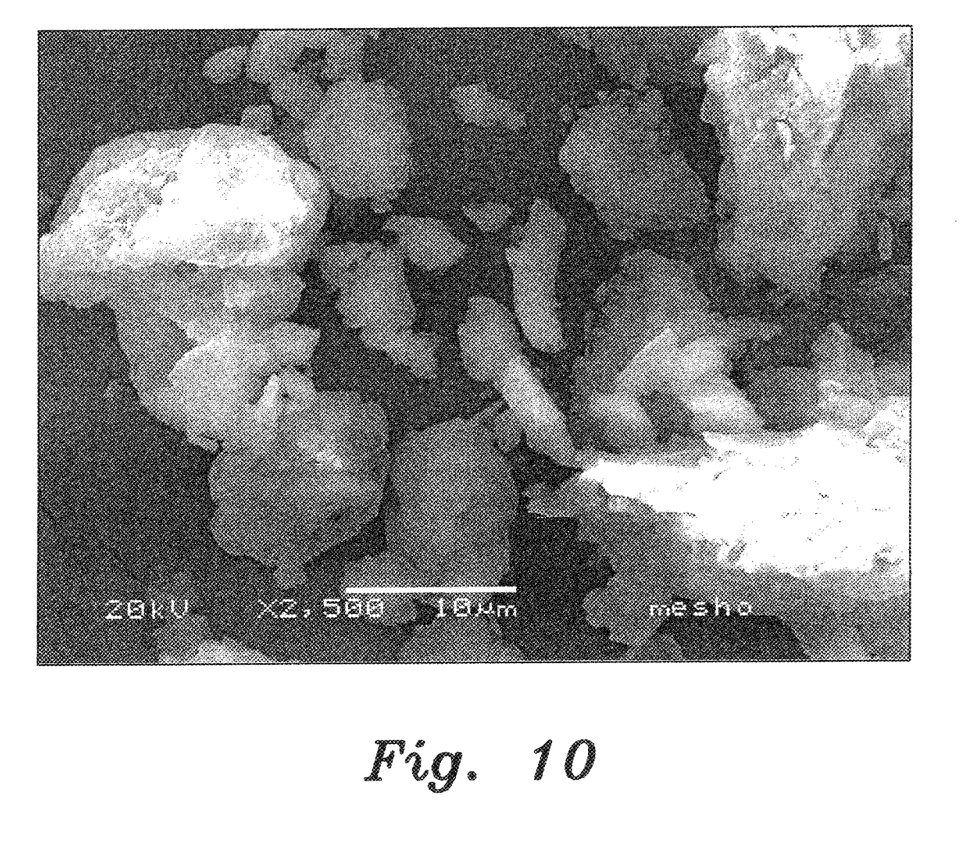
FIG. 10 is a scanning electron microscope (SEM) micrograph of Kholayis clay used in the method of using a clay suspension to prevent viral and phytoplasma diseases in plants according to the present invention.

FIG. 10 shows SEM micrograph of Kholayis clay, which includes a natural layered structure. Looking toward the bottom of the micrograph, the original micron-sized flaky clay particles with a pseudo-hexagonal morphology are apparent.

Figure 11A:
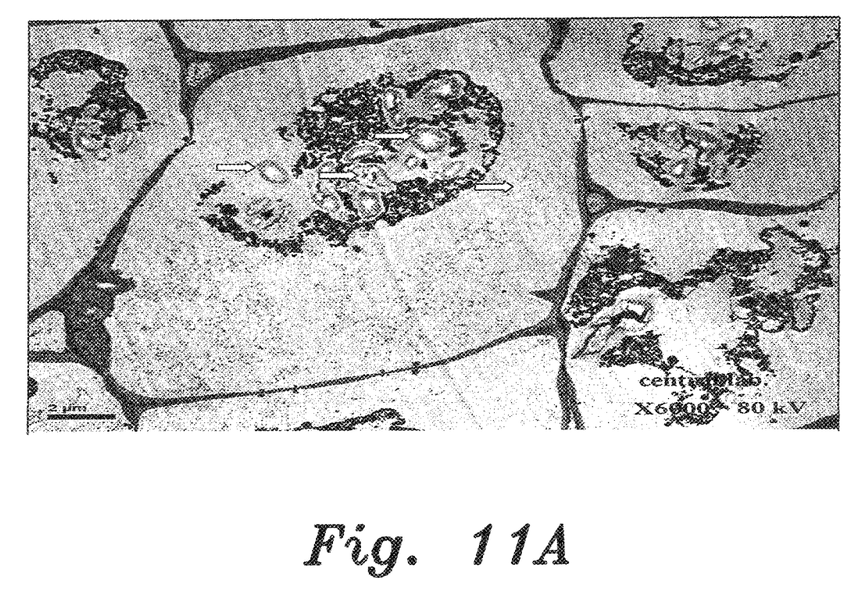
FIG. 11A is a transmission electron micrograph at low magnification by Transmission Electron Microscope (TEM) of a cross-section of lemon nursery shoots treated in a clay suspension (1% w/v) for one week, where the clay suspension is formed from clay in its natural state, showing phytoplasma cells with blowing, swelling pleomorphic units scattering inside the phloem.
Figure 11B:
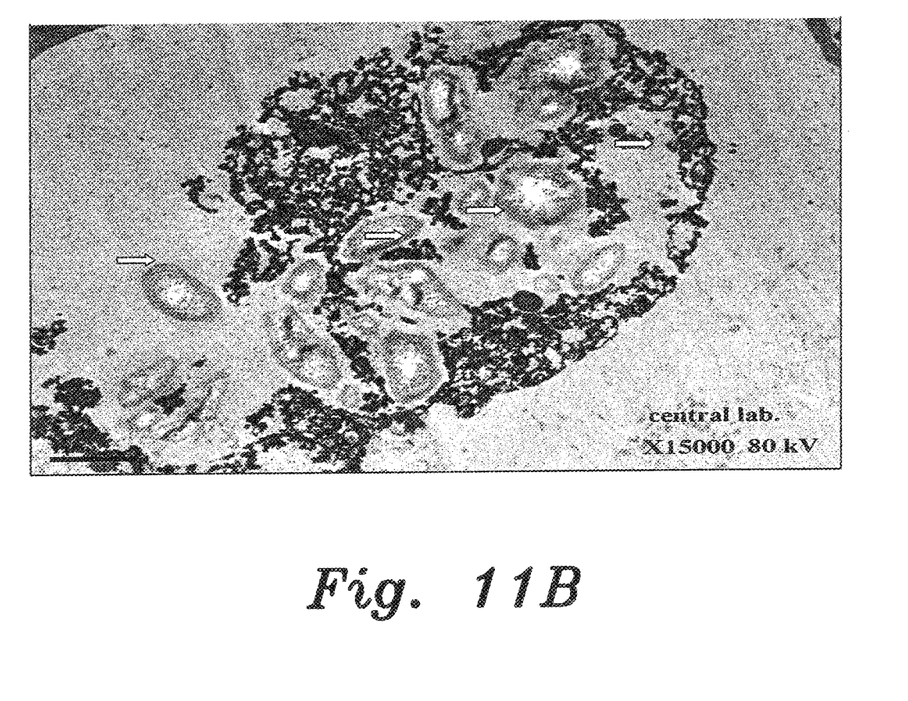
FIG. 11B is a transmission electron micrograph at high magnification by Transmission Electron Microscope (TEM) of a cross-section of the lemon nursery stick treated in the clay suspension (1% w/v) for one week.
Figure 12A:
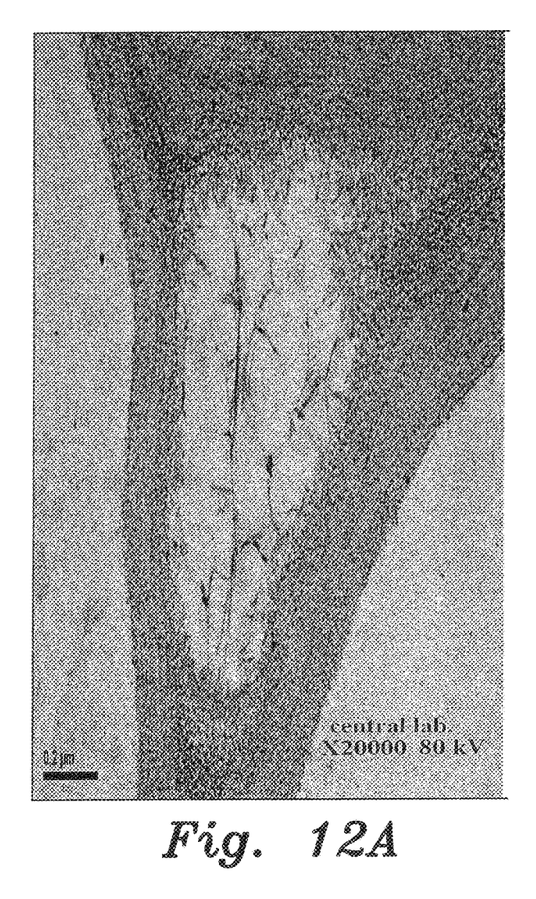
FIG. 12A is a transmission electron micrograph at low magnification by Transmission Electron Microscope (TEM) of the fibril structure inside the vesicular parts around an infected cell, with phytoplasma associated with clay particles.
Figure 12B:
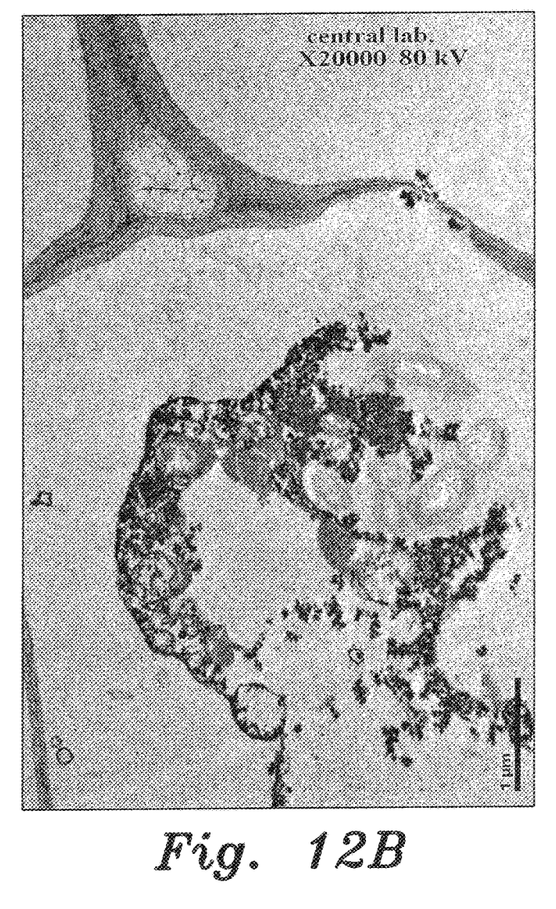

FIGS. 11A and 11B show TEM micrographs of cross sections of lemon nursery shoots infected with witches broom phytoplasma (treated and soaked in the clay suspension for one week), clearly showing phytoplasma cells with blowing, swelling pleomorphic units scattering inside the phloem. Phytoplasma cells dissolved upon incidence of the clay particles on the surface of the phytoplasma cells. FIGS. 12A and 12B show TEM images of fibril structures inside the vesicular parts around the infected cells, with phytoplasma associated with the clay particles.

The following example is illustrative only, and is not intended to limit the present teachings. Raw, untreated clay was collected in Jeddah, a northeastern province of Saudi Arabia. The clay was ground using a ball mill. The clay density was measured to be 2.5 g/cm$^3$=2.5×10$^6$ g/m$^3$. To form a 1% w/v clay suspension, 1.00 g of the clay in its natural state was placed in a graduated cylinder, and the volume was adjusted to 100 mL by adding distilled water. The cylinder was stoppered, followed by mixing of the suspension several times before use.

For a clay suspension formed from clay nanoparticles (i.e., nano-sized particles of the clay), fifty grams of clay was weighed and put in a 1.0 liter graduated cylinder. The cylinder was filled with distilled water. The cylinder was covered and then inverted three times to mix the clay with water. Then, the clay particles were left to separate and form sediment, at which point a timer was started. The desired diameter of clay nanoparticle was chosen as approximately 300 nm. The height of the clay suspension that was chosen to contain the desired clay nanoparticles was 4.0 cm. At the calculated time, using Stokes' law, the clay suspension was carefully removed using a large pipette. The clay suspension containing the clay nanoparticles was kept in the refrigerator. The suspension was stable for several months.

Principles of Stokes' law were relied upon for the nano sample preparation. The time was calculated based on the following equation:

$$t = \frac{18 n_0 h}{(\rho - \rho_0) g d^2},$$

where $n_0$ is the viscosity of water at 25° C.=0.89 g/m·s, h is the desired height of liquid suspension in the beaker, $\rho$ is the density of clay particles (2.5×10$^6$ g/m$^3$), $\rho_0$ is the density of water (1.0×10$^6$ g/m$^3$), g is the specific gravity (9.87 m/s$^2$) and d is the diameter of the clay particles.

For separation of the clay nanoparticles with an average size of about 300 nm, a rough estimate of sedimentation time to obtain 300 nm=300×10$^{-9}$ m clay particles, given by the Stokes' equation, is $$t = \frac{18 \times \left(0.89 \frac{g}{m \cdot s}\right) \times 0.04 \text{ m}}{(2.5 - 1.0)(10^6 g/m^3) \times 9.81 \text{ m/s}^2 \times (300 \times 10^{-9} \text{ m})^2} =$$

$$4.84 \times 10^5 \text{ s} = 5.6 \text{ days} = 5 \text{ days} + 14 \text{ hours} + 24 \text{ minutes.}$$

The height of 4 cm contains a range of clay nanoparticles in suspension. To calculate the smaller size of clay particles in the upper 0.02 m of the graduated cylinder, the above equation was used by inserting t=4.84×10$^5$ s. The smaller nanoparticles were calculated to be about 200 nm in diameter.

It is to be understood that the present invention is not limited to the embodiments described above, but encompasses any and all embodiments within the scope of the following claims.

We claim:

1. A method of using a clay suspension to inhibit tobacco mosaic virus infection in *Datura Metel* plants, comprising the step of administering an effective amount of a composition consisting of a suspension of Kholayis clay particles in water at 1% w/v to a *Datura metel* plant wherein said amount is effective to inhibit said virus infection on said plant.

2. The method of using a clay suspension to inhibit tobacco mosaic virus infection in *Datura metel* plants according to claim 1, wherein the step of administering the clay suspension to the *Datura metel* plant comprises administering the clay suspension to at least one outer surface of the plant.

3. The method of using a clay suspension to inhibit tobacco mosaic virus infection in *Datura metel* plants according to claim 1, wherein the Kholayis clay suspension consists of Kholayis clay nanoparticles in water at 1% w/v.

4. The method of using a clay suspension to inhibit tobacco mosaic virus infection in *Datura metel* plants according to claim 3, wherein the clay nanoparticles each have diameters between approximately 200 nm and approximately 300 nm.

* * * * *